United States Patent [19]

Casberg et al.

[11] 4,349,493
[45] Sep. 14, 1982

[54] BRIQUETS OF HYDRATED CALCIUM HYPOCHLORITE

[75] Inventors: John M. Casberg, Cheshire; Clair H. Putnam, Madison, both of Conn.

[73] Assignee: Olin Corporation, New Haven, Conn.

[21] Appl. No.: 219,089

[22] Filed: Dec. 22, 1980

Related U.S. Application Data

[63] Continuation-in-part of Ser. No. 956,543, Nov. 1, 1978, abandoned.

[51] Int. Cl.³ .................................................. B01J 2/00
[52] U.S. Cl. ..................................... 264/37; 264/117; 264/109
[58] Field of Search .......................... 264/109, 117, 37

[56] References Cited
U.S. PATENT DOCUMENTS 2,023,459  12/1935  Bachman ......................... 252/187 H
2,729,855  1/1956   Titus et al. ........................... 264/109
3,342,674  9/1967   Kowalski ............................... 424/14
3,424,842  1/1969   Nürnberg ............................. 264/109
3,544,267  12/1970  Dychdala ................................ 23/86
3,669,894  6/1972   Faust .................................... 252/187
3,956,444  5/1976   Kibbel, Jr. ........................... 264/109

Primary Examiner—James R. Hall
Attorney, Agent, or Firm—James B. Haglind; Donald F. Clements

[57] ABSTRACT

A novel briquet is comprised of compressed hydrated calcium hypochlorite particles having a calcium hypochlorite content in the range from about 55 to about 75 percent by weight, a water content in the range from about 4 to about 10 percent by weight and a compression strength of from about 2 to about 95 kilograms. The briquets may be used in sanitizing water supplies as they dissolve slowly to release available chlorine at a controlled rate.

6 Claims, 6 Drawing Figures

BRIQUETS OF HYDRATED CALCIUM HYPOCHLORITE

This application is a continuation-in-part of co-pending application U.S. Ser. No. 956,543, filed Nov. 1, 1978, now abandoned.

This invention relates to novel product forms of calcium hypochlorite. More specifically, this invention relates to briquets of hydrated calcium hypochlorite.

Calcium hypochlorite is a well known source of "available chlorine" for sanitation purposes, for example, in disinfecting the water of swimming pools. Calcium hypochlorite is added to the water to maintain a small residual of "available chlorine", suitably from about 0.5 to about 1.5 parts per million parts of water, which is generally sufficient to insure prompt destruction of bacterial contamination, so that the water is safe to swim in.

Anhydrous calcium hypochlorite compositions having a $Ca(OCl)_2$ concentrations of about 70 percent by weight have been available in granular or tablet form to be added to the swimming pool water to provide the desired levels of available chlorine.

Commercial tabletting of calcium hypochlorite is limited to calcium hypochlorite particles whose size is greater than 200 microns. Smaller particles or fines abrade the dies and punches and calcium hypochlorite compositions containing more than about 1 or 2 percent of these particles cannot be employed in tabletting operations. Thus small particles and fines which are generated during, for example, drying of calcium hypochlorite must be collected, compacted, and granulated before they can be tabletted.

More recently, hydrated calcium hypochlorite compositions have been developed having a water content of 4 percent by weight or greater which are more resistant to ignition and exothermic decomposition than the anhydrous product. Tabletting of calcium hypochlorite having a water content of above 3 percent by weight cannot be accomplished efficiently in commercial tabletting apparatus as caking of the punches results in excessive wear of the equipment. Frequent shutdowns for maintenance of the equipment are required and product control with respect to both the uniformity and the appearance of the tablets is difficult to maintain.

One object of the present invention is to provide a novel product form of hydrated calcium hypochlorite compositions.

Another object of the present invention is to provide a process producing hydrated calcium hypochlorite products which can employ small or fine particles.

An additional object of the present invention is to provide a product form of hydrated calcium hypochlorite compositions having improved active chlorine release properties for sanitizing water supplies.

A further object of the present invention is to provide a product form of hydrated calcium hypochlorite compositions having improved handling and shipping properties.

These and other objects of the invention are accomplished in a briquet comprised of hydrated calcium hypochlorite compositions having from about 55 to about 75 percent by weight of $Ca(OCl)_2$, a water content of from about 4 to about 10 percent by weight, and the briquet having a compression strength of from about 2 to about 95 kilograms.

Figure 1:
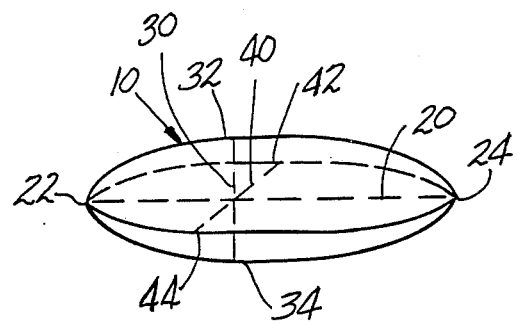
FIG. 1 shows a descriptive side view of a briquet of the present invention.

FIG. 1 shows a descriptive side view of briquet 10 in which major axis 20 has edge 22 at one end and edge 24 at the opposite end. Minor axis 30 has edge 32 at one end and edge 34 at the opposite end. Lateral axis 40 has edge 42 at one end and edge 44 at the opposite end. Edges 32 and 34 at opposite ends of minor axis 30 and edges 42 and 44 at opposite ends of lateral axis 40 have portions which are substantially straight and are parallel to each other and to major axis 20.

Figure 2:
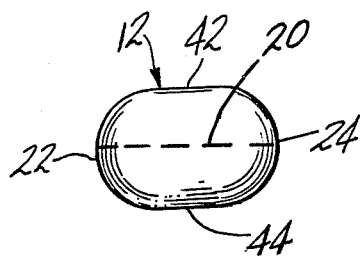
FIG. 2 illustrates a top view of another embodiment of a briquet of the present invention.

FIG. 2 illustrates a top view of briquet 12 in which sides 42 and 44 have substantially straight portions which are parallel to each other and to major axis 20. Edges 22 and 24 have a slight curvature. As shown in the side view (FIG. 3), edges 32 and 34 have substantially straight portions which are parallel to each other and to major axis 20.

Figure 4:
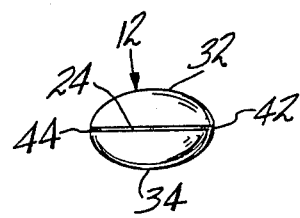
FIG. 4 depicts an end view of the briquet of FIG. 2.

FIG. 4 depicts an end view in which the biconvex curvature of briquet 12 is shown.

Figure 5:
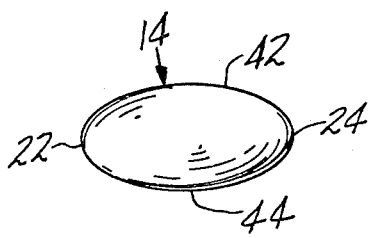
FIGS. 5 and 6 show top views of additional embodiments of briquets of the present invention.

In the embodiment shown in FIG. 5, briquet 14 has no substantially straight portions along edges 22, 24, 42, and 44.

Figure 6:
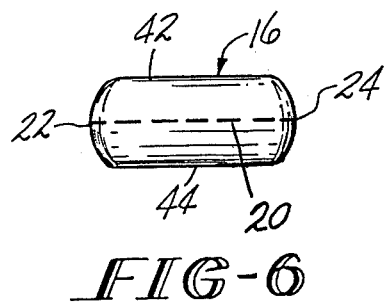

FIG. 6 illustrates a top view of briquet 16 in which the major portions of edges 42 and 44 are substantially straight and parallel to each other and to major axis 20.

More in detail, the briquets of this invention are prepared from particles of solid, hydrated calcium hypochlorite containing from about 55 to about 75 percent and preferably from about 65 to about 72 percent by weight of calcium hypochlorite, $Ca(OCl)_2$, and from about 4 to about 10 percent and preferably from about 5 to about 8 percent by weight of water, the balance being inert materials usually resulting from the process of manufacture, e.g. sodium chloride, calcium hydroxide, calcium chloride and calcium carbonate. The hydrated calcium hypochlorite has a specific gravity of about 2.1 to about 2.2. Hydrated calcium hypochlorite particles of this type may be produced by known processes such as those described in U.S. Pat. No. 3,544,267 issued on Dec. 1, 1970, to G. R. Dychdala or U.S. Pat. No. 3,669,894 issued on June 13, 1972, to J. P. Faust.

Briquets of the present invention may be produced from particles of hydrated calcium hypochlorite of any suitable particle sizes. For example, briquets can be made entirely of "fines", i.e. particles in the size range of from about 20 to about 200 microns in diameter, or from granular sized particles.

Preferably, the briquets are produced from a mixture of fines and granular particles as the fines fill in the voids between granular particles and provide the briquet with increased strength. Suitable particle sizes include those in the range of from about 20 to about 2,500 microns, and preferably from about 50 to about 1,000 microns. Where mixtures are employed, the fines can make up from about 5 to about 90 percent of the mixture, and preferably from about 15 to about 70, and more preferably from about 25 to about 50 percent by weight of the mixture.

In the process of the present invention for producing the novel briquets, particles of hydrated calcium hypochlorite are conveyed to a feeding device. The feeding device can be of any suitable type including those which discharge a controlled amount of particles by gravity flow or those employing pressure means, for example, a feed screw. From the feed device, the particles are fed to a briquetting device such as a roll briquetting press having matching briquet-forming pockets. The particles fill the gap between the rolls and are drawn or forced into the roll pockets. A preselected pressure, i.e., hydraulic, pneumatic or spring pressure, is exerted against the particles between the rolls and briquets of the desired shape and size are produced. Any suitable roll pressures may be used in producing the briquets, for example, roll pressures of from about 500 to about 3000 pounds per square inch (from about 35 to about 210 kilograms per square centimeter) are satisfactory although higher or lower pressures may be used if desired. The briquets fall from the pockets of the roll as the rolls move from the gap and are collected below the rolls.

Following release from the pockets, the briquets are preferably fed to a device which removes rough edges, i.e., "flashing" from the briquets and separates uncompacted fines. Any suitable "deflashing" means may be used which is capable of removing flanges or excess material from the edges and separating and recovering fine particles of hydrated calcium hypochlorite. Deflashing produces briquets with low attrition to fines during handling and shipping. Deflashed briquets recovered from the deflashing device are ready for packaging or direct use. Fine particles of hydrated calcium hypochlorite recovered from the deflashing step may be recycled to the feeding device.

Figure 3:
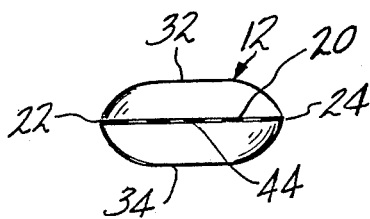
FIG. 3 represents a side view of the briquet of FIG. 2.

The finished briquets may be of any suitable shape. Generally ellipsoidal solids having the shape, for example, of that of a pillow, almond, or egg are preferred. More preferred are pillow shaped briquets of the type illustrated in FIGS. 2-4 and 6 having sides which are substantially uniform in width and where the curvature at the ends is slight. Pockets on the briquetting rolls which have a slight curvature at the ends are easily filled and the briquets formed undergo reduced stress during compaction. It is also advantageous if the briquets have portions of edges 32 and/or 34 as illustrated in FIGS. 1 and 3 which are parallel to major axis 20 of the briquet. Where both edges 32 and 34 have portions parallel to major axis 20, they are also parallel to each other. Edges 42 and/or 44 may also have portions parallel to major axis 20. For example, edges 32 and/or 34 and 42 and/or 44 may be parallel to the major axis for a distance ranging from about 0 to about 90, preferably from about 10 to about 90, and more preferably from about 30 to about 70 percent of the length of the major axis.

During compaction, the parallel portions aid in distributing compression stresses so that the finished briquets are more resistant to splitting or breaking.

Hydrated calcium hypochlorite briquets of the present invention may be of any suitable size. For example, suitably sized are briquets whose length along major axis 20 is at least about 1.2 times, preferably from about 1.5 to about 3 times the length along minor axis 30, and whose length along major axis 20 is at least 1.2, preferably from about 1.2 to about 2 times the length along lateral axis 40.

To prevent excessive breakage or attrition during handling and shipping, the finished briquets should have a suitable compression strength. Compression strength may be determined by using a compression tester such as a RIMAC Spring Tester (Reinck-McIlwaine, Inc. DuMont, N.J.). In using this testing device to determine the compression strength, a briquet is held in place between an upper and lower platform of the apparatus. A slow even force is applied to the briquet by lowering the upper platform at a rate of no greater than about 10 pounds per second. Force is continually applied until the briquet cracks or splits. The force required for cracking the briquet is shown on an indicator. Suitable finished briquets of hydrated calcium hypochlorite compositions having a weight of from about 5 to about 8 grams have a compression strength of in the range of from about 2 to about 95 kilograms, and preferably from about 45 to about 75 kilograms.

Briquets of hydrated calcium hypochlorite of this invention have favorable solubility characteristics as they dissolve slowly to release available chlorine at a controlled rate. By producing briquets having a bulk density in the range from about 1100 to about 1450 and preferably from about 1170 to about 1360 kilograms per cubic meter, considerable savings are realized in packaging costs over those of tabletted materials. Briquets require less packing space than tablets for an equal weight of hydrated calcium hypochlorite. The briquets also produce low amounts of fines during shipping and handling and are much more readily removed from drum containers than tablets, for example, by using a scoop. Their smooth surface presents a pleasing appearance.

The novel process of the present invention permits the use of a wide range of particle sizes for hydrated calcium hyphoclorite. Fines and small particles unsuitable for processes such as tabletting can be employed directly without using granulation methods.

Although briquetting of hydrated calcium hypochlorite does not require an additive such as a binding agent or a lubricant, one may be used, if desired.

The following Examples are presented to further illustrate the invention without any intention of being limited thereby. All parts and percentages are by weight unless otherwise specified.

EXAMPLE 1

Hydrated calcium hypochlorite granules [98.8 percent being in the particle size range of −16 to +70 mesh (212 to 1180 microns)] were added to a screw feeder operating at a rate of 60 rpm. The feeder continuously supplied the hydrated granules to a roll compactor (K-G Industries Compacting Press) operating with a roll pressure of 700 pounds per square inch, a roll gap of about 0.010 inches and rotating at a speed of 40 rpm. As the briquets were produced they were passed down a chute onto a vibratory screening device (SWECO Vibro-Energy Finishing Mill) which removed flanges and uncompacted hydrated calcium hypochlorite. Oval pillow shaped briquets of the type of FIGS. 2-4 having a parallel edge along the upper and lower surfaces (55 percent of the length) were recovered from the screener. The briquets had an average weight of 6.9 grams, a volume of 3.6 cubic centimeters, a compression strength of 77 kilograms, and a bulk density of 1201 kilograms per cubic meter. A drop test was conducted in which samples of 10 briquets were placed in a cup and poured all at one time onto a cement floor from heights of 4 feet and of 6 feet. The briquets were then examined for breakage or extensive chipping at each of these heights, all 10 of the briquets in each sample passed the drop test.

EXAMPLE 2

The procedure of Example 1 was repeated using hydrated calcium hypochlorite granules [90 percent in the particle size range of −12 to +35 mesh (500 to 1700 microns)] in which 0.1 percent by weight of stearic acid had been admixed. The oval pillow shaped briquets produced were those of FIGS. 2-4. They had an average weight of 7.15 grams, a volume of 3.47 cubic centimeters and a compression strength of 47.2 kilograms. In the drop test, 9 of 10 briquets passed at a height of 4 feet and 8 of 10 briquets survived at a height of 6 feet.

EXAMPLE 3

The procedure of Example 1 was repeated with a fee composed of 80 percent of granular material (90 percent being in the particle size range of −12 to +35 mesh) and 20 percent being fines recycled from the SWECO screener. Oval pillow shaped briquets were produced having an average weight of 7.14 grams, a volume of 3.57 cubic centimeters and a compression strength of 50.8 kilograms. In the drop test, all briquets passed at a height of 4 feet, while 3 briquets failed at the height of 6 feet.

EXAMPLE 4

Hydrated calcium hypochlorite fines, having a Ca(OCl)$_2$ content of about 65 percent by weight and a water content of 5.8 percent by weight were fed to a roll compactor. The compactor was equipped with a screw feeder operating at 30 rpm. Fine particles were continuously fed between rolls maintained at a pressure of 1500 pounds per square inch and a roll speed of 15 rpm to produce oval pillow shaped briquets of the type shown in FIGS. 2-4. The briquets had an average weight of 7.52 grams, a volume of 3.62 cubic centimeters and a compression strength of 61.5 kilograms. Screen analysis of the fines is as follows:

| Sieve Size (microns) | Wt. % | Wt. % CUM. |
| --- | --- | --- |
| −1180 + 600 | .3 | .3 |
| −600 + 300 | 11.2 | 11.5 |
| −300 + 150 | 29.8 | 41.3 |
| −150 + 75 | 38.4 | 79.7 |
| −75 + 45 | 14.6 | 94.3 |
| −45 | 5.7 | 100.0 |

EXAMPLE 5

Rectangular pillow shaped briquets of the type of FIG. 6 were produced from the hydrated calcium hypochlorite fines used in Example 4. The compactor was operated at a roll speed of 40 rpm applying a roll pressure of 800 psi. Briquets produced had an average weight of 6.88 grams, an average volume of 3.6 cubic centimeters and a compression strength of 35.8 kilograms.

EXAMPLE 6

A jar containing 8 liters of water at 30° C. was placed on a magnetic stirrer and the stirrer started. The rate of stirring was adjusted to give good stirring without forming a vortex. Fifty grams of hydrated calcium hypochlorite oval pillow shaped briquets, produced in accordance with this invention, were placed in a dissolving basket. The briquets had weights in the range of 6.8 to 7.2 grams, and bulk densities in the range of 1200 to 1362 kilograms per cubic meter. The dissolving basket was suspended from the jar rim, with the bottom of the basket at a depth sufficient to completely immerse the briquets in the water. The time of immersion was recorded. Samples of water (10 ml) were taken periodically and titrated with sodium thiosulfate to determine the available chlorine content. When the tablets were completely dissolved and no further increase in available chlorine concentration was found, the time was recorded. The solution rate for 50 grams of briquets of hydrated calcium hypochlorite was found to be between 7 and 8 hours. Thus briquets were produced having a slow solubility rate with the release of available chlorine at sanitizing concentrations over an extended period.

EXAMPLE 7

Briquets were produced from hydrated calcium hypochlorite comprised of 65.9% Ca(OCl)$_2$ and 6.4% water. The briquets of the type of FIGS. 2-4 weighed 7.8 grams±0.1 grams and were produced at a roll pressure of 1100 psi at a roll speed of 23 rpm. Hydrated calcium hypochlorite briquets were placed on a grid in a tank of water where the grid was at a depth of 5–6 inches below the water surface in the tank. Tap water at a temperature of 31°±1° C. was circulated through the tank at a rate of 1 quart per minute. The rate of dissolution was visually observed and the time recorded when 95% by weight of the briquet had been dissolved. In each of three determinations, the dissolving times were found to be, respectively, 360 minutes, 360 minutes, and 300 minutes.

COMPARATIVE EXAMPLE A

Tablets of hydrated calcium hypochlorite comprised of 66.5% Ca(OCl)$_2$ and 6.5% water were hand pressed on a Carver press at 2,000 pounds per square inch. The round tablets weighed 7.8 grams±0.1 gram. Using the procedure of Example 7, the dissolution time for the tablets was determined. In each of three determinations, it was found that 95% of the tablets had dissolved after 80 minutes.

The novel briquets of the present invention employed in Example 7 have highly favorable solubility characteristics as they dissolve slowly to release their available chlorine. When compared with tablets containing identical amounts of hydrated calcium hypochlorite, the dissolving time for the briquets was increased from 275 to 350 percent over that of the tablets.

What is claimed is:

1. A process for producing briquets of hydrated calcium hypochlorite having from about 55 to about 75 percent by weight of Ca(OCl)$_2$, a water content of from about 4 to about 10 percent by weight, which comprises:
   (a) feeding particles of hydrated calcium hypochlorite to a briquetting means,
   (b) applying roll pressures in the range of from about 35 to about 210 kilograms per square meter to form briquets of said hydrated calcium hypochlorite particles, and
   (c) recovering said briquets from said briquetting means.

2. The process of claim 1 wherein said particles of hydrated calcium hypochlorite have particle sizes in the range of from about 20 to about 2,500 microns.

3. The process of claim 1 wherein said recovered briquets are fed to a deflashing means and uncompacted particles of hydrated calcium hypochlorite are separated from said briquets.

4. The process of claim 3 wherein said uncompacted particles are recovered and recycled to step (a).

5. The process of claim 4 wherein said hydrated calcium hypochlorate particles are comprised of from about 65 to about 72 percent by weight of $Ca(OCl)_2$ and said water content is from about 5 to about 8 percent by weight.

6. The process of claim 5 wherein said hydrated calcium hypochlorite particles have particle sizes in the range of from about 50 to about 1,000 microns.

* * * * *